(12) United States Patent  (10) Patent No.: US 7,991,165 B2
Kassal et al.  (45) Date of Patent: Aug. 2, 2011

(54) NOISE REJECTING ELECTRONIC STETHOSCOPE

(75) Inventors: James J. Kassal, N. Kingston, RI (US); Joseph S. Russotti, Norwich, CT (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1287 days.

(21) Appl. No.: 11/586,741

(22) Filed: Oct. 4, 2006

(65) Prior Publication Data

US 2008/0137876 A1  Jun. 12, 2008

(51) Int. Cl.
*A61B 7/04* (2006.01)

(52) U.S. Cl. .......................................... 381/67; 181/131

(58) Field of Classification Search .................. 381/67, 381/71.1–71.6, 71.8, 71.11, 150, 190; 181/126, 181/131–132; 73/431, 578; 600/300, 534, 600/528, 595, 538

See application file for complete search history.

(56) References Cited

U.S. PATENT DOCUMENTS

| | | | |
|---|---|---|---|
| 5,610,987 A * | 3/1997 | Harley | 381/67 |
| 5,844,995 A * | 12/1998 | Williams | 381/67 |
| 6,026,170 A * | 2/2000 | Dieken et al. | 381/67 |
| 6,295,365 B1 * | 9/2001 | Ota | 381/114 |
| 6,438,238 B1 * | 8/2002 | Callahan | 381/67 |
| 6,661,161 B1 | 12/2003 | Lanzo et al. | |
| 6,691,821 B2 * | 2/2004 | Oster et al. | 181/131 |
| 7,006,638 B1 * | 2/2006 | Baekgaard et al. | 381/67 |
| 2003/0208130 A1 | 11/2003 | Yotam et al. | |

* cited by examiner

*Primary Examiner* — Xu Mei
*Assistant Examiner* — Lun-See Lao
(74) *Attorney, Agent, or Firm* — Joseph K. Hemby, Jr.; Albert M. Churilla; Ning Yang

(57) ABSTRACT

An acoustic-electronic stethoscope that filters aberrant environmental background noise. The chest piece employs acoustic vents to inhibit resonant amplification of noise and contains a diaphragm design that focuses vibrational energy to a raised ring, which transfers and further focuses the energy to a piezoelectric polymer sensor with dual elements. The ensuing electrical signal is then preamplified with the low frequency sound, comprising predominantly background noise, filtered out. The stethoscope contains a binaural head set and output jack for down loading of data. Furthermore, areas normally subject to exposure and damage to water, such as the chest piece and headset, are water-tight.

27 Claims, 16 Drawing Sheets

ASSEMBLED VIEW

EXPLODED VIEW

CROSS SECTION OF ASSEBLY

NOTES:
1. FASTENERS SUCH AS RIVETS ARE USED WHERE INDICATED BY DASHED LINES TO FORCE ELECTRICAL CONTACT BETWEEN PIEZOELECTRIC POLYMER SENSOR ELEMENTS AND THE CIRCUIT BOARD.

2. APPROPRIATE ADHESIVE IS APPLIED TO GROOVED AREA OF CIRCUIT BOARD TO LAMINATE SENSOR ELEMENTS TO THE CIRCUIT BOARD.

EXPLODED VIEW

ASSEMBLED VIEW

NOISE REJECTING ELECTRONIC STETHOSCOPE

BACKGROUND OF INVENTION

1. Field of Invention

The inventive subject matter relates to an acoustic-electronic stethoscope capable of selectively amplifying sounds of medical importance while suppressing environmental background noises. The inventive stethoscope contains an innovative chest piece design and employs simplistic circuitry to emulate the sound quality of standard acoustic stethoscopes. The inventive stethoscope is rugged, water resistant, and simple to operate.

2. Description of the Related Art

Physicians and other health care workers use stethoscopes in order to evaluate sounds emanating from tissue sources, primarily heart and lung. Evaluation of these internal organs is via the transmission of the sound energy through the skin. Classic stethoscope design attempts to minimize the area of skin evaluated for sound transmission as well as minimizing the effects of outside environmental noise. However, with environments with increasing ambient noise, such as in busy hospitals and outside field settings, ambient environmental noise is becoming an increasing issue in the ability to properly discriminate and evaluate relevant sounds from background noise. Additionally, traditional acoustic stethoscopes introduce many distortions in its signal. Many of these distortions are the result of standing waves in the long tubes.

Non-traditional sensors that are adhered to the skin avoid some of the environmental noise distortions but they have relatively small output signals, which must be amplified. Thin-film piezoelectric materials adhered to skin can sense skin vibration caused by body sounds. Vibration of the skin causes minute flexion of the sensor that generates an electrical signal. However, adherent sensors present the user with several inconveniences including: patients with body hair must be shaved at all locations of interest; because of the adhesive, moving the sensor from location to location is slow and therefore not practical for even routine examinations; the user must take extreme care to avoid extraneous noise caused by anything that touches the sensor or its lead wire.

Noise sources that are problematic for all electronic stethoscopes include: environmental noise that couples into the sensor within the chest piece and is therefore mixed with sounds of interest before entering the electronic circuitry; noise that couples into the unit and gets conveyed to the user's ears through the head set tubes; environmental noise and mechanical vibrations that enter the patient through epidermal tissue and subsequently detected by the sensor; environmental noise that enters the user's ears directly; muscle tremor noise that is caused by holding the chest piece and detected by the sensor; electromagnetic pick-up (interference). While none of these can be totally eliminated, the present invention has design features that reduce most of them.

Attempts have been made to develop noise-tolerant stethoscope-like systems based on active noise-cancellation technology. These devices tend to be large and impractical for field use. And they have had limited success in reducing noise because upon entering the human body, noise characteristics are dramatically transformed in ways that differ substantially from person to person. It is therefore impossible to sample the environmental noise with a separate sensor and then subtract that noise from sounds of interest. Further their inherent complexity of design, such as the inclusion of an additional pick-up and electronics, adds cost and complexity, thus making these devices unsuitable for field use such as in the military or ambulance. Therefore, a need exists for sensitive, sound discriminating stethoscopes that are both rugged and simple and therefore less prone to mechanical failure, especially in field settings.

SUMMARY OF INVENTION

Currently available electronic stethoscopes are often complex in design. Furthermore, they typically amplify both ambient noise as well as the sounds of interest making them of limited use in environments that contain normally high background noises. An aspect of this invention, therefore, is a stethoscope that is simple and rugged in design but offers significant enhancement of medically important sounds over background environmental noise. Accomplishment of this design goal is partially met by preferentially amplifying sounds of interest over ambient background, rather than mere amplification of all sounds. The device has broad applicability especially in high noise areas, such as field clinics or naturally noisy areas such as ships, shipyards and factories.

Another object of the invention is an acoustic-electronic stethoscope wherein sound is transformed into an electrical signal generated by a piezoelectric sensor and where dual piezoelectric sensor elements generate electrical signals of opposite polarity.

Another object of the invention is a chest piece containing a plurality of acoustic vents that reduce resonant amplification of environmental sound.

A further object of the invention is a raised ring diaphragm for focusing sound vibration onto the piezoelectric sensor.

A still further object of the invention is an acoustic-electronic stethoscope wherein an electrical signal generated as a result of sound vibrations inducing dynamic strain in piezoelectric polymer sensor elements is passed through a preamplifier circuit that suppresses low frequency sounds.

An additional object of the invention is an acoustic-electronic stethoscope that is resistant to damage by water. The water-sensitive components of the stethoscope are sealed permitting the stethoscope to be operated under harsh weather conditions.

A still additional object of the invention is an acoustic-electronic stethoscope that provides, through the ear tips, audible signals that indicate when controls are accessed.

DETAILED DESCRIPTION AND PREFERRED EMBODIMENTS

Figure 1A:
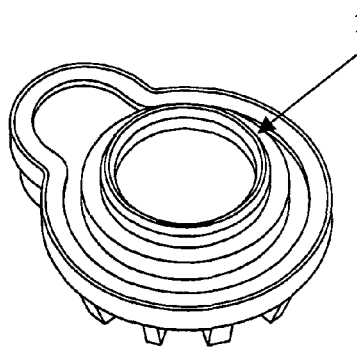
FIG. 1. Illustration of top and side view of diaphragm and diaphragm retainer.

The inventive aspect of this invention is a stethoscope with improved acoustical extraction of relevant sound by reducing detection of environmental (i.e. background) noise. A reduction in environmental noise is achieved by a combination of structural and electronic components that collectively maximize the signal to noise ratio. These include a novel diaphragm and diaphragm retaining structure of the chest piece. The chest piece includes vents that permits the region between the diaphragm and the sensor to be substantially acoustically unbounded and, therefore, minimizing creation of resonant cavities where ambient sound can be amplified. The inventive aspect also includes dual piezoelectric sensor elements providing signals of opposite polarity contained on a circuit board containing a plurality of deep grooves in both opposed surfaces on which the piezoelectric polymer sensor elements are mounted. The grooved structure of the circuit board permits flexion of that region of the circuit board and permits strain in the piezoelectric polymer sensor. The ensuing signals are then electrically filtered to suppress low frequency sounds, often due to muscle tremors or other sounds that tend to obfuscate visceral sounds, such as from the heart.

An aspect of the current invention is to increase the ratio of the signal of interest to ambient noise by concentrating the majority of vibrational force to a narrow area by molding a raised circular ring onto the diaphragm of the chest piece. The signal concentrated to this raised area of the diaphragm is then transferred to dual piezoelectric polymer sensing elements that generate analogous electrical signals. The inventive stethoscope also minimizes ambient noise by eliminating the need for venting behind the speakers, contained in the earpieces. Interference by environmental noise is further minimized by arranging the earpieces such that when in place on the wearer, they are coaxial. This feature permits optimal sealing between the earpiece tips and the wearer's ear canals.

Collectively, an electrical signal with reduced noise is achieved by the transfer of vibrational energy, focused onto the raised area of the diaphragm. Minimization of ambient noise is further achieved by the provision of vents around the chest piece that minimize the creation of resonate sound. A coupling disk then transfers the vibrational energy to a sensor assembly with grooved structures to permit flexion of the assembly and generation of a piezoelectric signal. The signal is then transferred to a circuit board for amplification and further conditioning. Additional reduction in ambient noise is provided by an improved headset design that places the two ear tips coaxially when in place on the wearer. This configuration affords an optimal seal and further reduces environmental noise.

The inventive stethoscope is ideal for field settings by not only affording a reduction in ambient noise but also having water resistant properties. Water resistance is provided in the chest piece by the inclusion of seal assembly between the diaphragm and the sensor assembly. Furthermore, compliant air volume that is required for operation of most speakers is provided by the sealed air volume between the micro speaker and the junction box. This design improvement eliminates the need to vent to the environment, which would concomitantly expose the device to damage from water.

The inventive stethoscope is contemplated to be able to be configured in a number of ways. However, to better illustrate the inventive concepts, the following examples are provided to better illustrate the stethoscope components.

Example 1

Diaphragm and Diaphragm Retainer Assembly

Figure 1B:
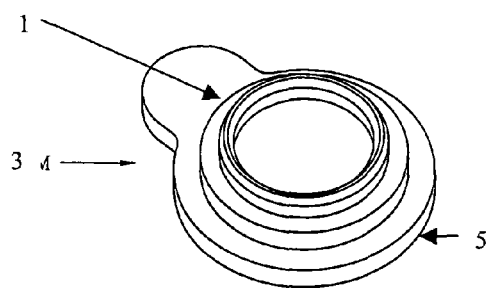
Figure 1B:
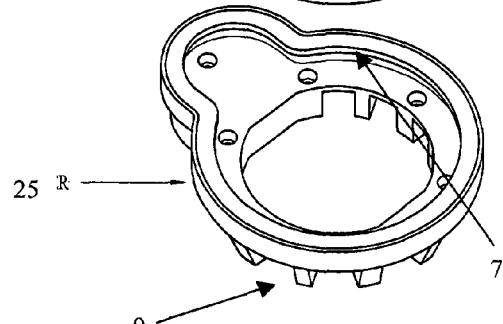
Figure 1C:
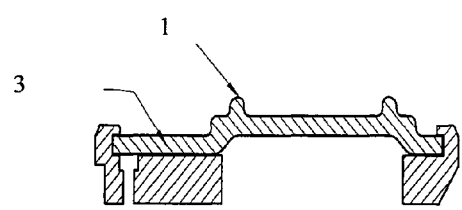
Figure 2A:
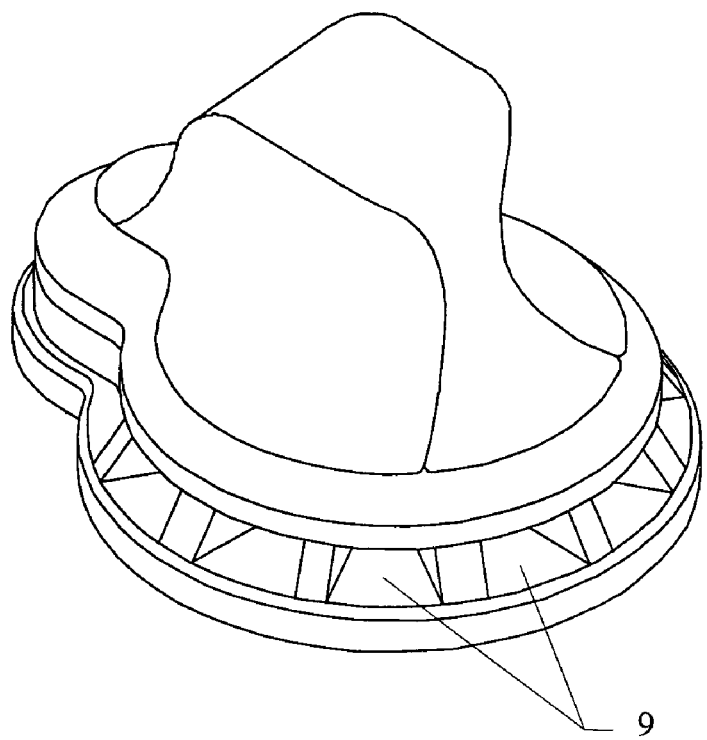
FIG. 2. Illustration of chest piece and coupling disk.

An example and preferred embodiment for the design of the diaphragm component of the chest piece, the reader is referred to FIG. 1A. In FIG. 1A, a raised circular ring (1) is molded directly into the diaphragm (3). The majority of vibrational energy impacting onto the diaphragm is concentrated on the raised circular ring (1), which is ultimately transferred to a sensor assembly containing piezoelectric sensor elements resulting in an electrical signal. The ring also forms a circular node for surface vibrations of the skin, notably those vibrations that arise from interaction between the skin and environmental sound. The diaphragm (3) is made from a flexible material, such as Santoprene or Polyurethane, and contains an outer edge (5) that fits into and is firmly held in place by an undercut groove (7) contained in the diaphragm retainer (25) FIG. 1B. For patient comfort, a preferred embodiment is for the diaphragm retainer (25) to be made of a non-metallic material, such as plastic. A detailed illustration of the physical association between the diaphragm and the diaphragm retainer is shown in FIG. 1C. Furthermore, the diaphragm retainer contains a series of acoustic vents (i.e. spaces) illustrated in FIG. 1 and FIG. 2A (9). Although any number of vents can be incorporated into the chest piece, the vents must be large and numerous enough so that the interior portion of the chest piece between the diaphragm/diaphragm retainer and the sensor assembly is substantially acoustically unbounded around the perimeter. Therefore, these acoustic vents prevent a resonant cavity from being formed within the interior of the chest piece bounded by the sensor preventing concomitant amplification of ambient sound. As an example of a preferred embodiment, the chest piece contains 10 vents around perimeter. However, the invention contemplates chest pieces with more or less vents and vents of various sizes.

Figure 2B:
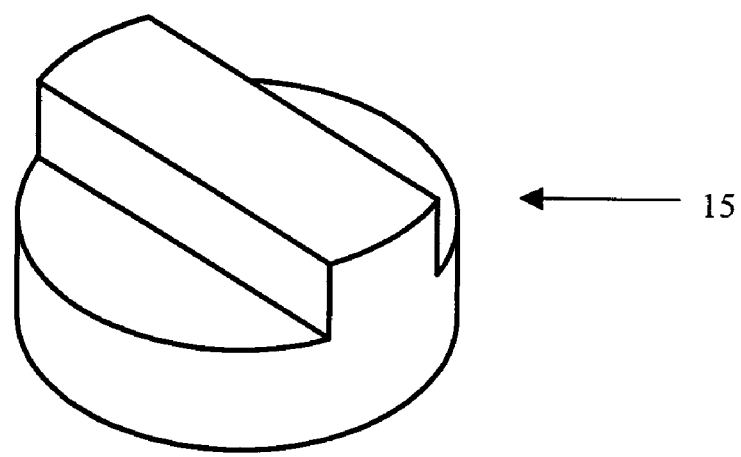
Figure 3:
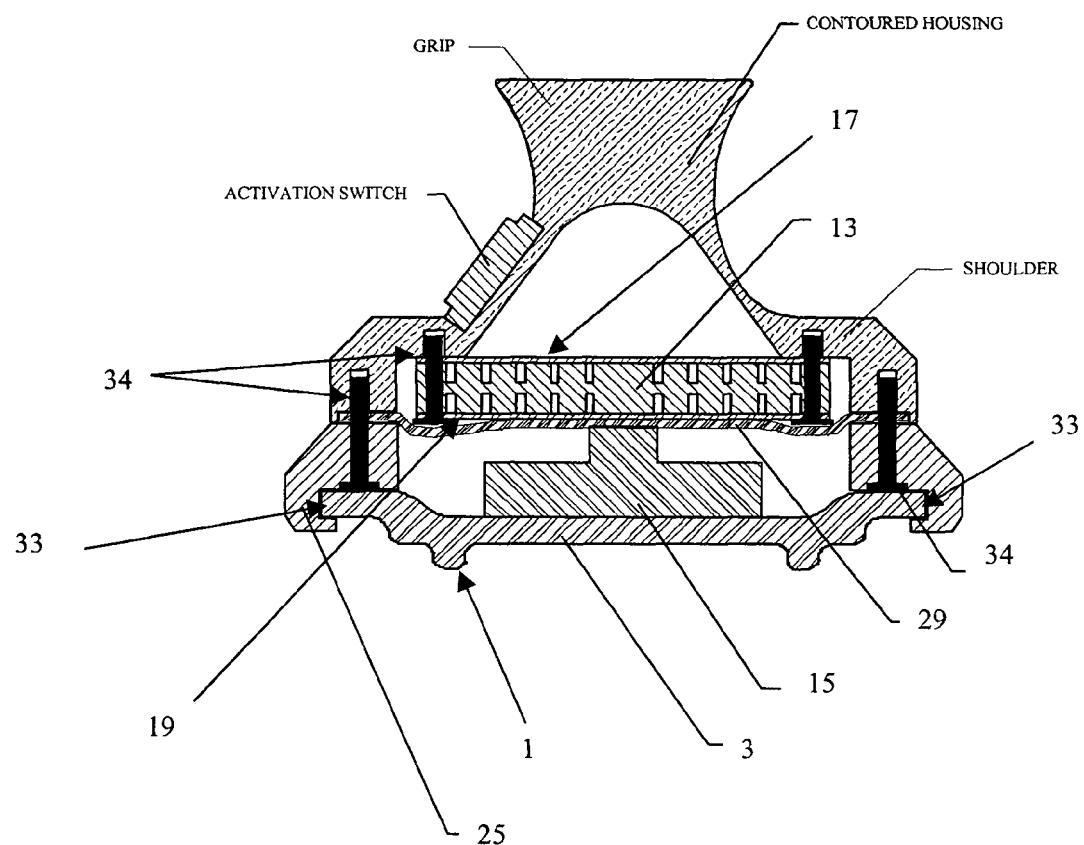
FIG. 3. Exploded view of chest piece and sensor assembly.

The vibrational energy is transferred from the diaphragm to piezoelectric materials yielding detectable electrical signals. Referring to FIG. 3, in a preferred embodiment, the vibrational energy from the diaphragm (3) obtained through the raised circular ring (1) of the diaphragm (3) (FIG. 1) is transferred to a sensor assembly (13) via a coupling disk (15) (FIG. 2B). The vibrational energy transferred from the diaphragm (3) to the coupling disk (15) is concentrated onto the center of the sensor assembly (13) (FIG. 3). While the center of the sensor assembly is moving upward, in response to vibrational energy supplied by the coupling disk (15), the inner piezoelectric polymer sensor element (17) attached to the sensor assembly (13) experiences increasing tensile strain while the outer piezoelectric polymer sensor element (19) experiences decreasing tensile strain. These changing piezoelectric polymer material strains give rise to electrical signals of opposite polarity which then enter a differential preamplifier built into the circuit board (FIG. 6) (21) of the sensor assembly (13) and are amplified for subsequent signal conditioning by signal conditioning circuitry.

Another example of stethoscope design incorporates a contoured housing with a grip portion that is shaped to minimize the effort required to hold it. This feature is illustrated in FIG. 3. The user can hold the chest piece between thumb and index finger or preferably between the index and middle fingers. The latter gripping method permits placement of the fingertips against the skin during use. The concave contour of the grip is an important ergonomic feature of the preferred embodiment of the chest piece design since it minimizes muscle tremor in the fingers, which further reduces noise.

Additionally, in another example also illustrated in FIG. 3, the activation switch (38) is placed in the concave portion of the grip at an approximately 45-degree angle. The angle enables a large portion of the force exerted to the chest piece during application to the patient to be applied through the switch. This enables the user to activate and deactivate the unit as the chest piece is moved from place to place during operation without squeezing the grip. This mimics use of a non-electronic stethoscope and avoids the need for the user to turn the power on at the start of an exam and off after the exam is completed. This feature also further reduces noise due to muscle tremor. The example feature further serves to protect the switch from inadvertent activation when the stethoscope is not in use since only objects of finger size and shape can fit into the area of the switch.

Example 2

Piezoelectric Sensor

Figures 4, 5:
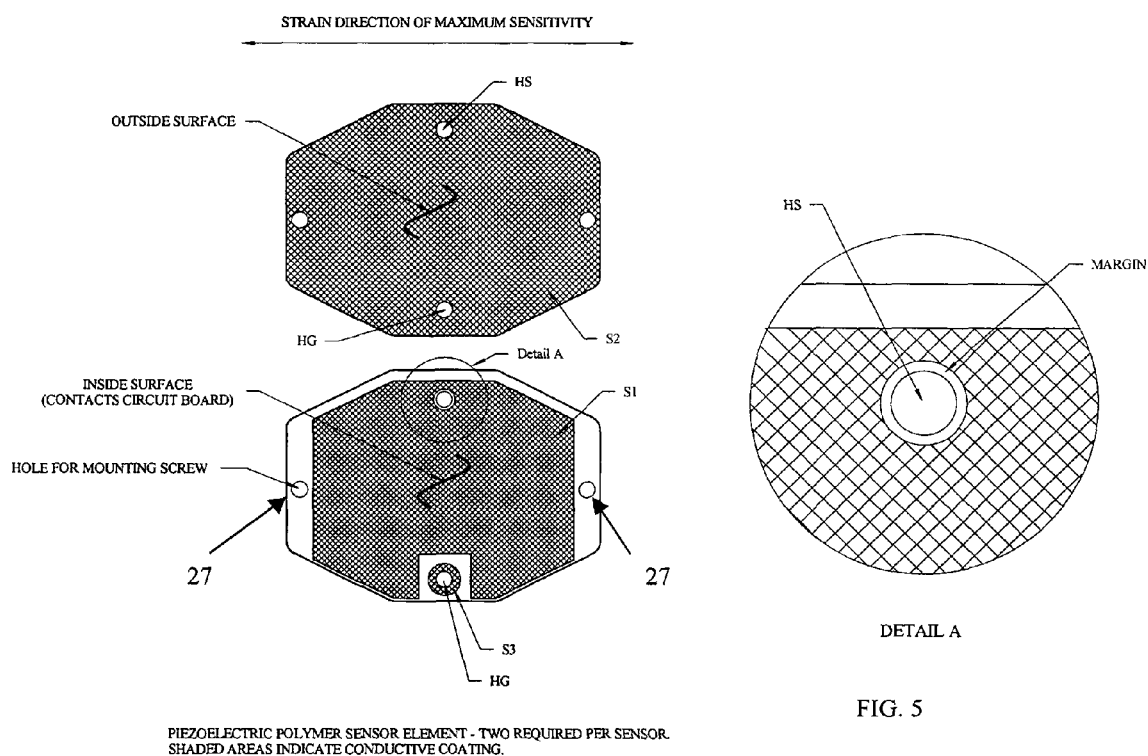
FIG. 4. Illustration of piezoelectric polymer sensor element.
FIG. 5. Expanded view of hole (HS) through sensor element, further illustrated in FIG. 4.

Although the piezoelectric polymer sensor elements can be designed in any number of configurations, a preferred configuration is illustrated in FIG. 4. Furthermore, the piezoelectric polymer sensor can be made from any number of materials exhibiting piezoelectric properties. However, as an example, a preferred embodiment is the use of polyvinylidene fluoride (PVDF).

As shown in FIG. 4 the piezoelectric polymer sensor elements each contain three conducting areas with the shaded areas illustrating conductive coating. Area S1 on the inside surface carries the voltage signals that are generated. Area S3 on the inside surface is electrically connected to area S2 by an number of conductive means, as indicated by HG. Conducting area S2 covers the entire outside surface and serves as one part of a Faraday shield of the sensor assembly. Hole HS through area S1 is surrounded by a margin, as illustrated in FIG. 5. The margin prevents inadvertent electrical contact between S1 and a fastener that is passed through HS in sensor assembly. Also, each of the piezoelectric polymer sensor elements has a preferred sensing direction (i.e., stretch axis) as indicated in FIG. 4.

Figure 6:
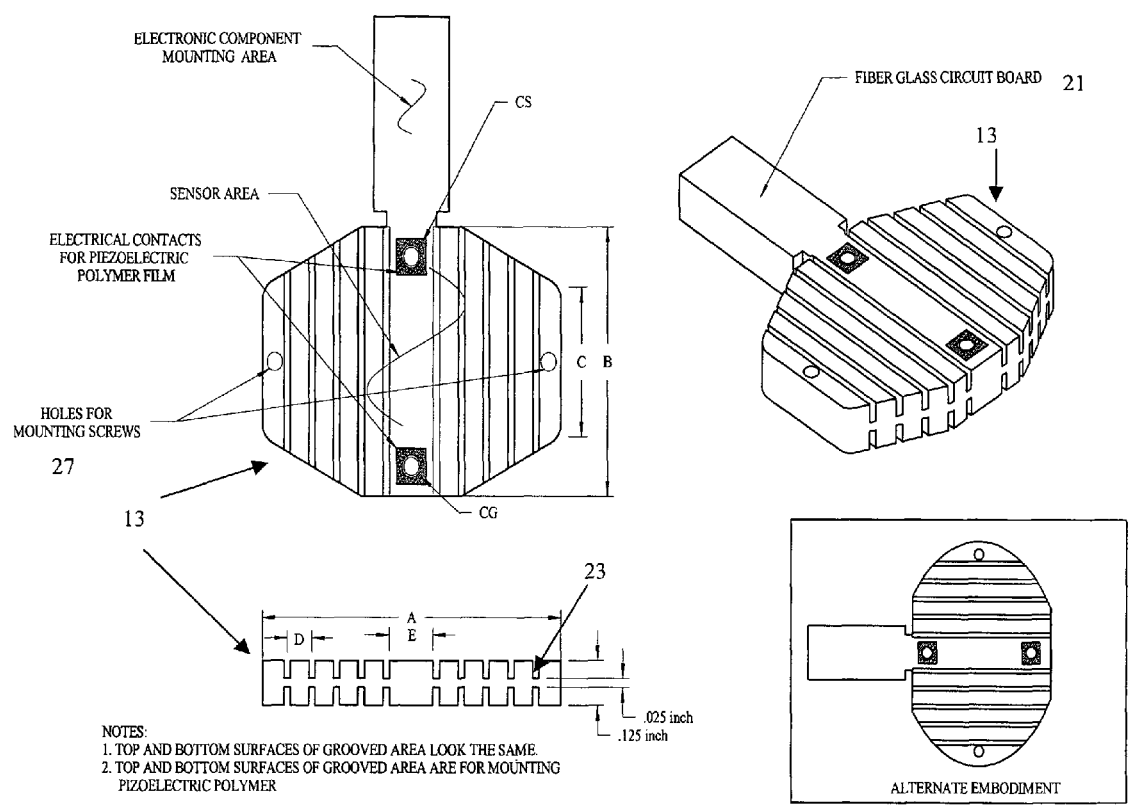
FIG. 6. Illustration of sensor assembly circuit board and grooved areas.
Figure 7:
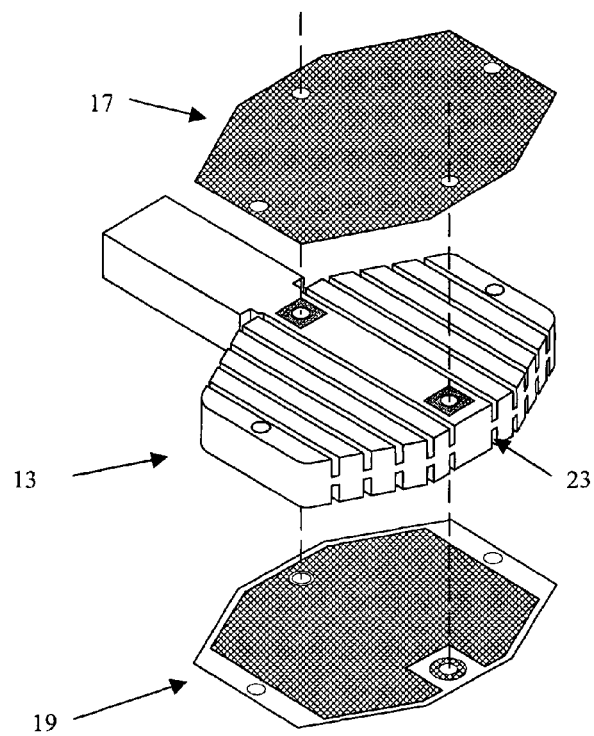
FIG. 7. Exploded view of sensor subassembly illustrating placement of piezoelectric sensors.

The arrangement of the sensor assembly can be any number of configurations. An example of a preferred configuration is shown in FIG. 6 and FIG. 7. In order to enable proper flexion of the sensor assembly (13) with electrical conduction following piezoelectric sensor strain, a number of designs are contemplated. However, common to these designs is the incorporation of a plurality of deep grooves areas (23) in both opposed surfaces of the sensor circuit board assembly on which the piezoelectric sensor elements are mounted. Referring to FIG. 6, in a preferred embodiment, the groove depth is such that they have the same depth on both sides and are as narrow as possible. The depth of the grooves is preferably such that the circuit board material thickness between the grooves is approximately 0.015 inches. The separation of grooves (D) is preferably adjusted to provide at least ten grooves across the sensor area. The space between the two center-most grooves (E) may be larger than the rest but is preferably less than two times the separation (D).

Two piezoelectric polymer sensor elements (17) and (19) are illustrated in FIG. 7 and are attached, preferably via adhesive, to a sensor circuit board assembly (13) to form a sensor assembly. Referring to FIG. 6 as well as FIG. 4 and FIG. 7, the configuration of the sensor circuit board assembly and piezoelectric polymer sensor elements is coordinated such that there is an assurance of contact between the electrical contact area CS (on the sensor circuit board assembly) and S1 (on each of the piezoelectric polymer sensor elements) and the electrical contact area CG (on the sensor assembly) and S3 (on each of the piezoelectric polymer sensors). Two fasteners are used to compress the piezoelectric polymer sensor elements against the sensor assembly to ensure electrical contact between CS and S1 and between CG and S3 of each of the piezoelectric polymer sensor elements.

Example 3

Chest Piece

The chest piece contains the following basic elements: housing; diaphragm and diaphragm retainer (see Example 1); coupling disk; seal membrane and tube fitting. The chest piece also includes the sensor assembly containing two sensor elements and a circuit board containing grooves (see Example 2), as well as easy to access controls, such as the on/off switch (12).

The sensor assembly (i.e. sensor circuit board assembly plus piezoelectric polymer sensor elements) is mounted together in the chest piece assembly with the coupling disk and diaphragm retainer containing the diaphragm. An example of a preferred embodiment of the mounting is illustrated in FIG. 3. As illustrated in FIG. 3, the sensor assembly is mounted on two shoulder areas of a contoured housing by means of fasteners passing through the holes (27), illustrated in FIGS. 4 and 6. Referring to FIG. 3, the diaphragm retainer (25) is secured to a contour in the housing (33) by a series of fasteners (34). Additionally, a seal membrane (29) is mounted over the sensor assembly. The function of the seal membrane (29) is to keep contaminants out of the inner compartment, containing the sensor assembly, of the chest assembly. The coupling disk (15) is mounted with adhesive to the diaphragm.

Therefore, referring to FIG. 3, electrical signal induction is provided by the transfer of vibrational energy, focused onto the raised circular ring (1) molded into the diaphragm (3), to the coupling disk (15). Acoustic vents (9), illustrated in FIG. 1, molded into the diaphragm retainer (25) minimize ambient environmental sound. The coupling disk then transfers vibrational energy from the diaphragm (3) to the center of the sensor assembly (13) causing flexion, facilitated by grooves (23), cause concomitant increase in tensile strain of the inner piezoelectric polymer sensor element (17) and decrease in tensile strain on the outer piezoelectric polymer sensor element (19) with ensuing induction of electrical signals of opposite phase. The electrical signals thereon are transferred to a preamplifier contained on the sensor circuit board.

Example 4

Processing of Piezoelectrial Signal

Electrical signals resulting from dynamic strains in the piezoelectric polymer sensor elements are transferred to a preamplifier located on the sensor assembly circuit board (21). A high pass filter pole at the input is provided to suppresses low frequency sounds, due largely to muscle tremor that would otherwise tend to obfuscate visceral sounds of interest. Additionally, in a preferred embodiment of the invention, the sensor assembly circuit board amplifier also contains a difference-amplifier that adds the flexure-generated signals (of opposite polarity) from the inner and outer piezoelectric polymer sensor elements and cancels, by subtraction, common mode noise from the sensor assembly. Common mode noise can arise from electromagnetic pick-up in the high impedance piezoelectric polymer sensor elements and also from acoustic noise that enters through vents and is incident directly on the piezoelectric polymer sensor elements.

Figure 8:
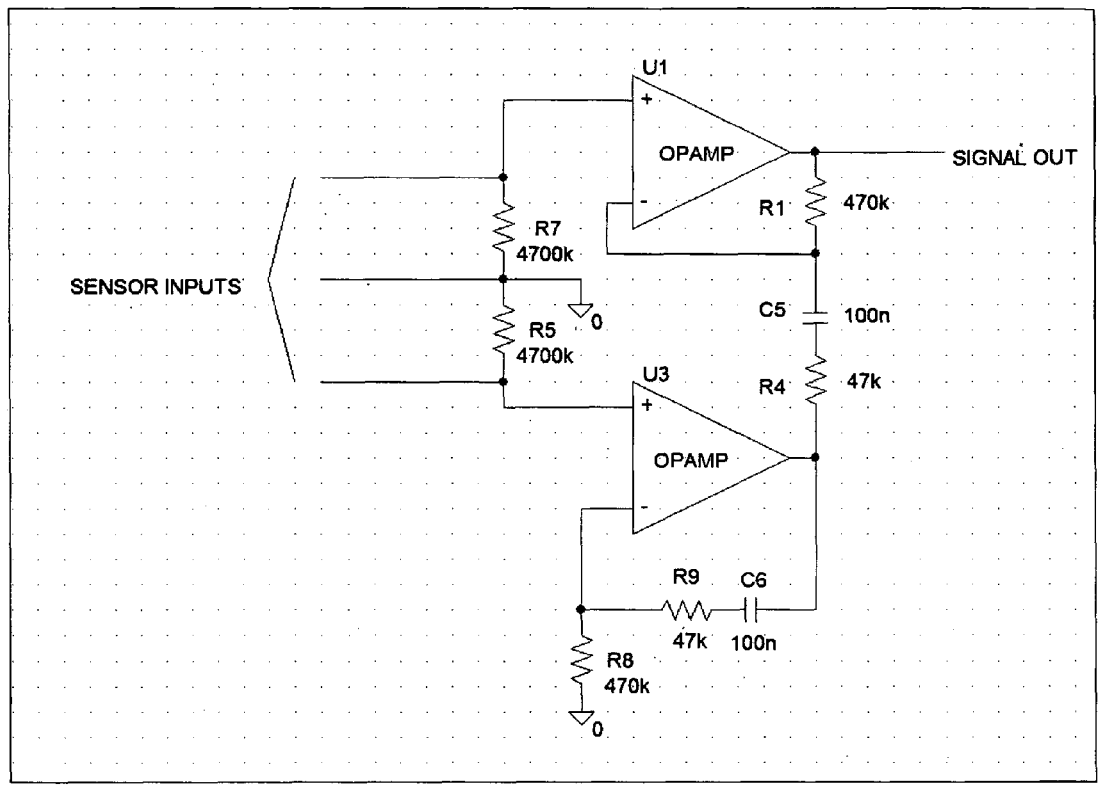
FIG. 8. Illustration of preferred embodiment of preamplifier circuit configuration.
Figure 9:
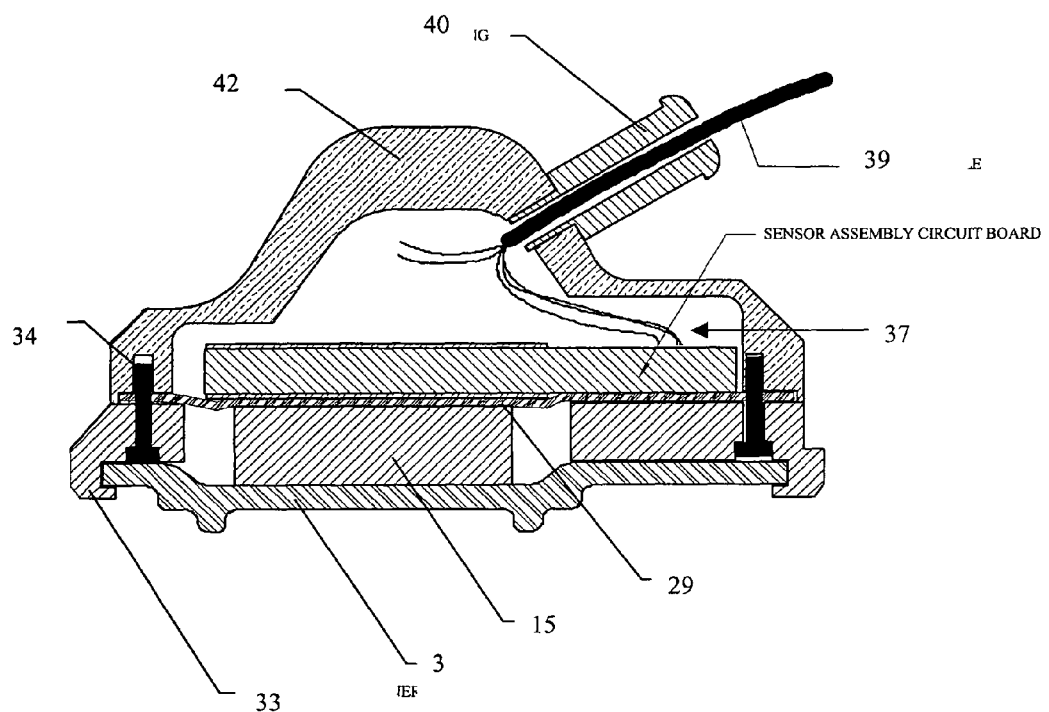
FIG. 9. Side view of chest piece illustrating barbed fitting and wire placement.
Figure 10:
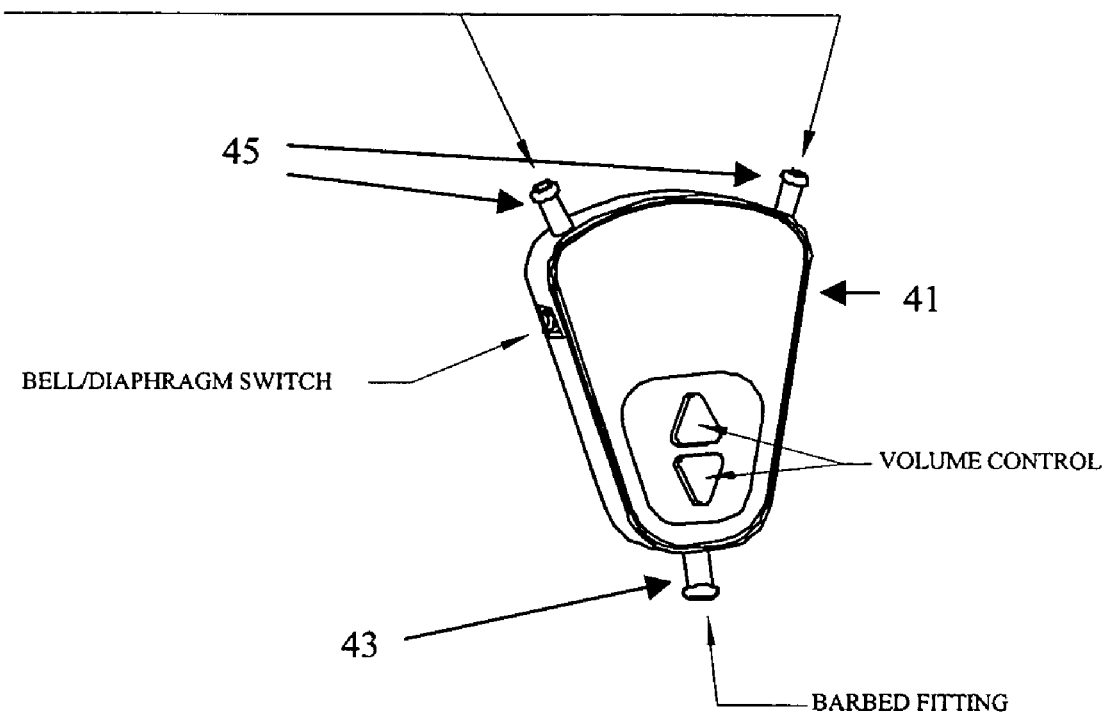
FIG. 10. Illustration of junction enclosure.

Although a number of preamplifier circuit configurations are envisioned, an example of a preferred embodiment of a preamplifier circuit configuration is illustrated in FIG. 8. As illustrated in FIG. 8, the circuit incorporates high pass filtering by including capacitors, C5 and C6, in feedback loops and also by employing a value for both the resistances R5 and R7 that, in combination with the series capacitance of the piezoelectric polymer sensor elements, provides a high pass filter pole at the input. Referring to FIG. 9 the electrical output of the preamplifier is then connected to a main circuit by means of a wire (37) that runs as a part of a wire bundle (39) from the chest piece to the junction enclosure where the main circuit board resides. Other wires, carrying battery power to the preamplifier and wires from the activation switch also run between the chest piece and the junction enclosure. Illustrated in FIG. 9 is a lengthwise vertical cross-section of the chest piece showing a barbed fitting (40) for attaching protective rubber tubing containing the bundled wires. The cable exits the chest piece through this fitting and is protected from damage by a length of thick insulating material, such as rubber, that serves to mechanically connect the chest piece to the junction enclosure (41) (FIG. 10). Also illustrated in FIG. 9 is the preferred embodiment of a contoured housing (42).

Figure 11:
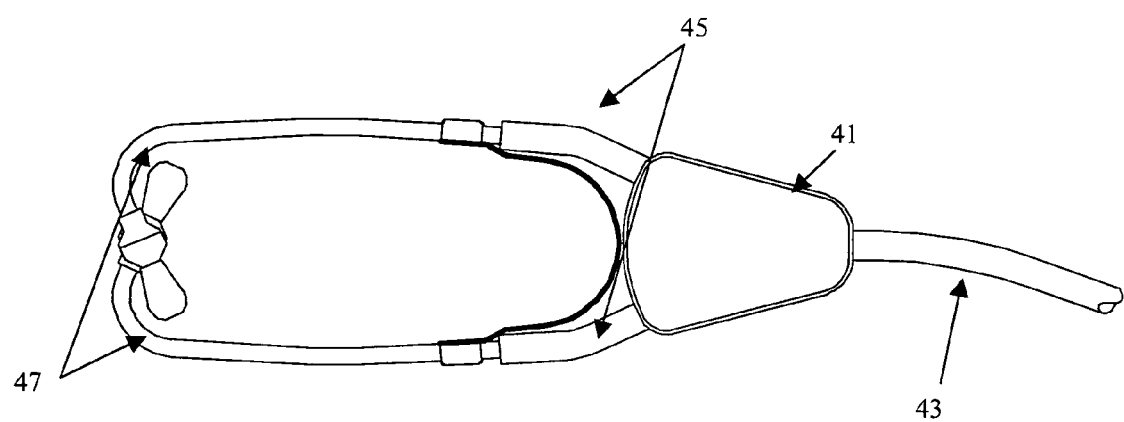
FIG. 11. Illustration of head set assembly and interrelationship connection with junction enclosure.

Referring to FIG. 10, the junction enclosure (41) contains three barbed fittings for rubber tubing. One fitting accepts the tubing from the chest piece (43). Two other fittings (45) attach the tubing of the binaural head set (47) (FIG. 11). The junction enclosure (41) contains the signal conditioning circuitry, batteries, and controls. In a preferred embodiment, the controls include volume controls and the switch for selecting either the bell or diaphragm mode. These modes are similar to the sound quality of the two types of heads of traditional acoustic stethoscopes. The bell mode emphasizes to lower frequency sounds of interest while the diaphragm mode enables the user to concentrate more on higher frequencies by suppressing pickup of lower frequencies that, when too loud, make it difficult to discern subtle higher frequency sound. Additionally, in order to prevent dust and other contaminants, the battery hatch contains an o-ring seal.

In a preferred embodiment, the invention contains two sets of high pass filters. When the bell mode is selected, the filter in use has a −3 dB frequency (cut-off) set to 55-65 Hz and when the diaphragm mode is selected, the cut off frequency is 90-100 Hz. The filters are preferably selective with a slope of 24 dB/octave below the cut-off. The frequency content above 100 Hz is virtually identical for both filters.

Figure 12:
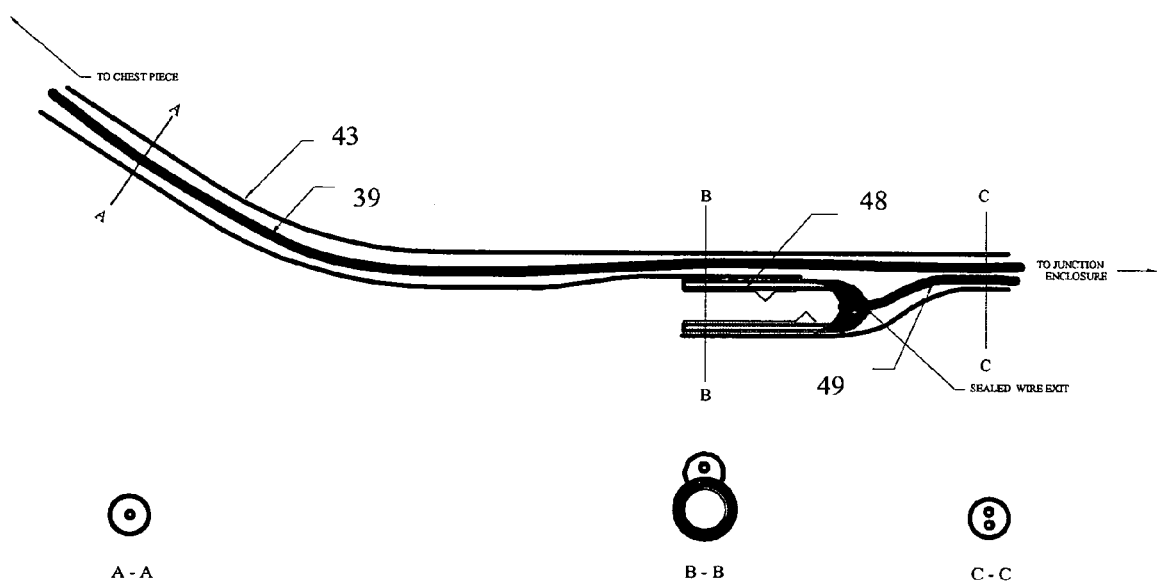
FIG. 12. Illustration of interrelationship of chest piece connecting tube and output jack.

Connection of the chest piece to the junction enclosure is via flexible protective tubing that contains the wires. Referring to FIG. 12, in a preferred embodiment, an output jack is located between the junction box and the chest piece. The jack enables connection of a wire to a recording device. The location of the jack permits convenience by minimizing the presence of the wire while operating the stethoscope. The output jack is electrically connected to the junction box via a pair of bundled wires (49), which then diverge in the output jack (48). A pliant mounting minimizes stress on the jack and mated plug and reduces electrical noise due to movement of the mated mechanical contacts common with a rigid mount. Additionally, the base of the jack and wires are sealed such that water is unable to inadvertently enter the jack and subsequently pass into the junction enclosure.

Example 5

Headset Assembly

Figure 13:
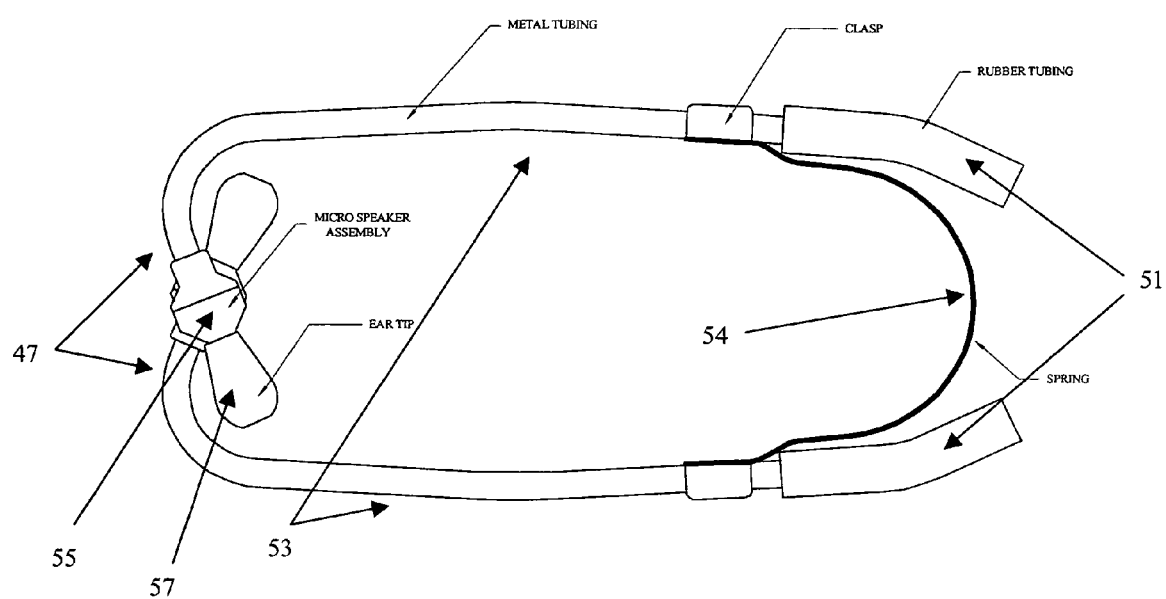
FIG. 13. Illustration of head set assembly-showing interrelationships of micro speaker assembly, ear tips and spring clasp.
Figure 14:
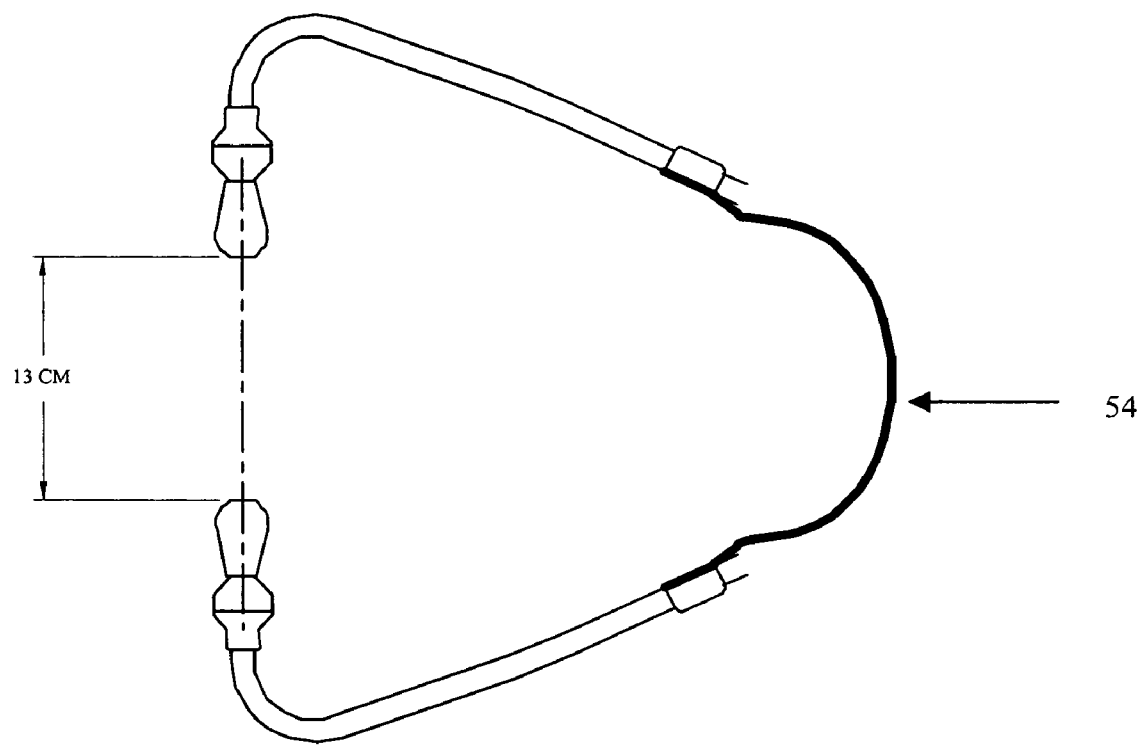
FIG. 14. Illustration of coaxial alignment when ear tips are extended.

An example of a preferred configuration of the binaural headset assembly is illustrated in FIG. 13. The assembly comprises two short lengths of rubber tubing (51) and two shaped pieces of metal tubing (53) and two micro-speaker assemblies (55) with ear tips (57). The metal tubing (53) is connected by a spring clasp (54). Although the size of the headset can vary, a preferred embodiment of the head set is such that when expanded the tips (57) are 13.0 cm apart, the two ear tips are coaxial when the metal tubes (53) are rotated within the spring clasps (54) to allow the ear tips to point towards each other. This is illustrated in FIG. 14. This size is preferably selected since the average distance between ear tips when a stethoscope is used, along with the coaxial feature, affords the best seal between the ear tips and the ear canal of the operator in order to exclude environmental noise.

Figure 15A:
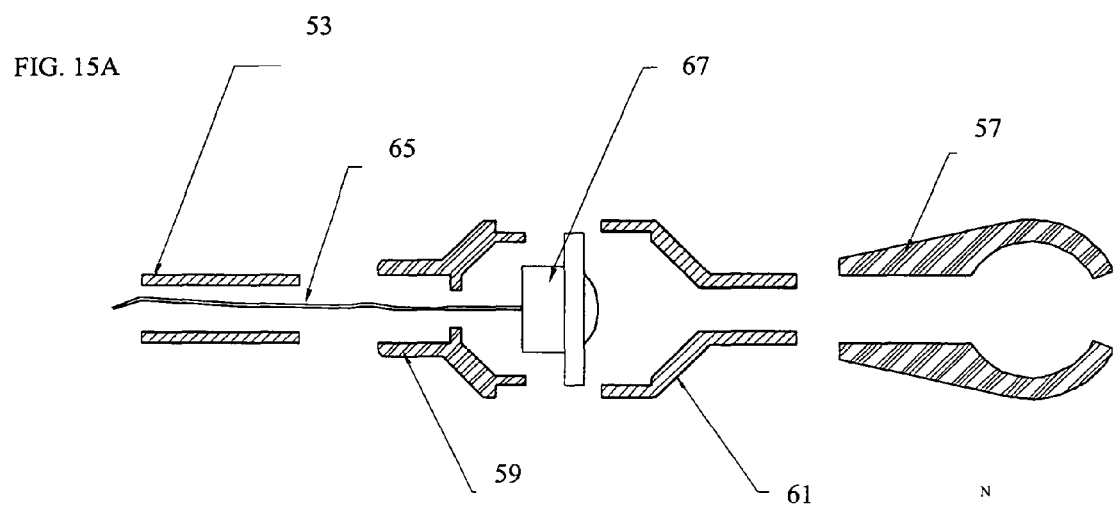
FIG. 15. Illustration of interrelationship of micro speaker and ear tip assembly showing air volume supplying micro speaker.
Figure 15B:
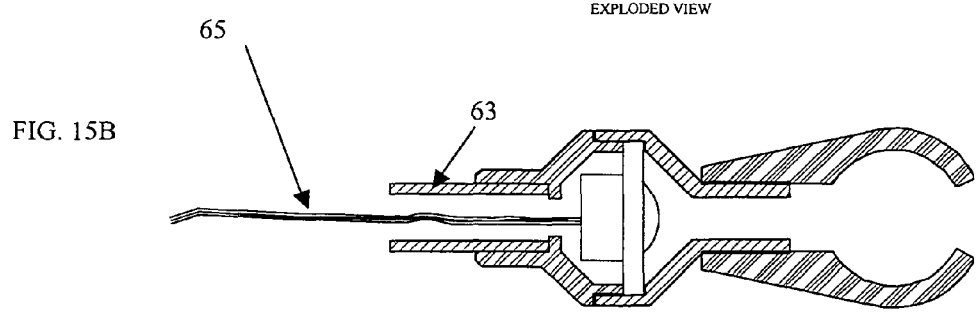

The micro-speaker assembly is illustrated in FIG. 15 showing exploded (FIG. 15A) and assembled views (FIG. 15B). The rear housing section (59) and forward housing section (61) has features that clamp the micro-speaker in place as seen in the assembled view. After insertion of the ear tip (57) (FIG. 14) into the user's ear canal, the micro-speaker, forward housing (61), ear tip (57), ear canal and eardrum form a sealed volume of air.

Figure 16:
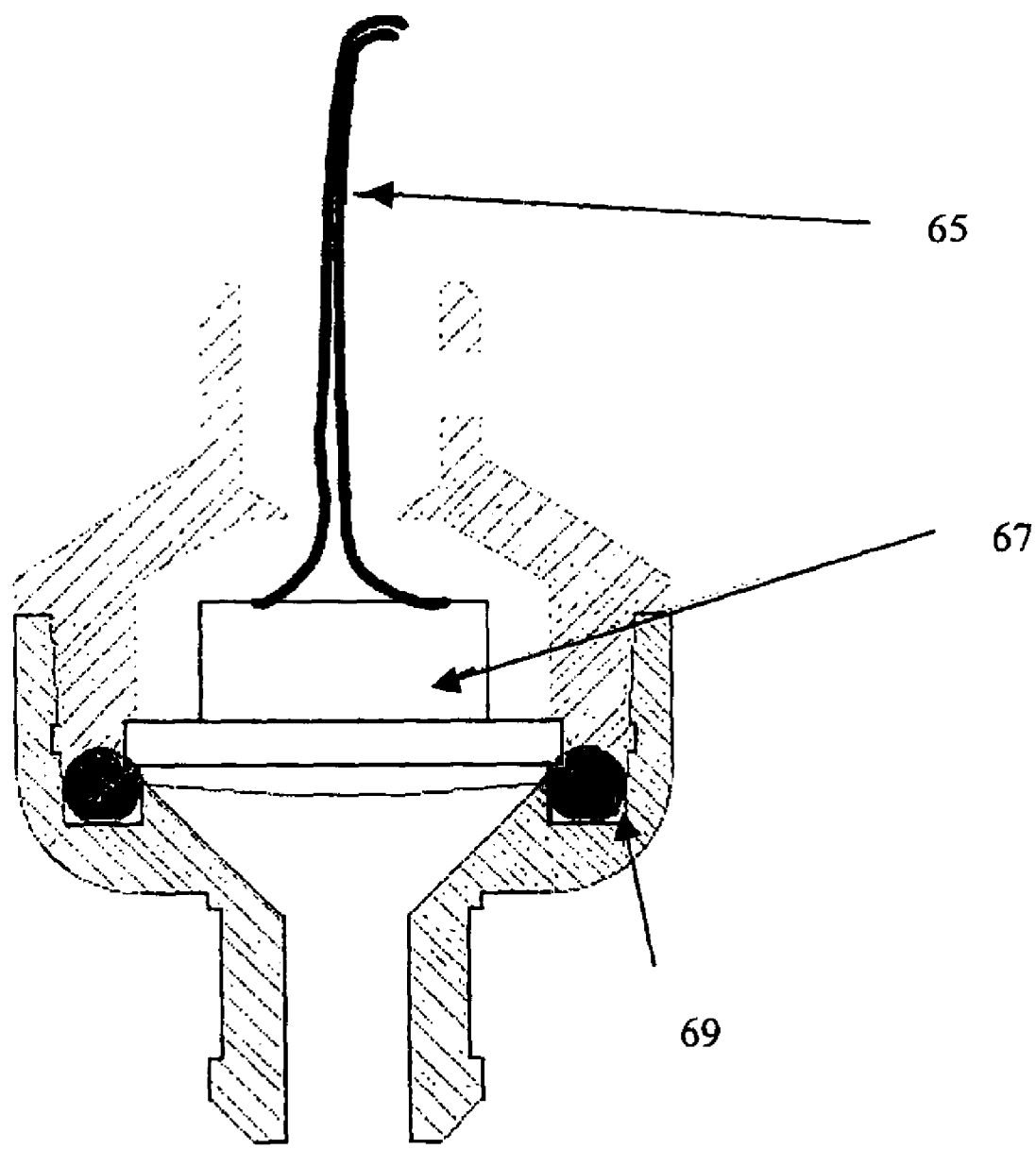
FIG. 16. Side view of speaker assembly illustrating O-ring assembly sealing speaker from outside environment.

The rear housing section (59) has an opening (63) for the speaker wire (65) and the size of the opening is sufficiently large as to present a relatively large volume of air extending from the speaker (67) through the tubing to the barbed fitting (45) of the junction enclosure, as illustrated in FIG. 15. The air volume permits the air between the speaker and the junction box to serve as compliant volume, without the possibility of contamination of dust or water, which is required for proper operation of the speaker. As illustrated in FIG. 16, the speaker (67) is sealed from the environmental by an O-ring assembly (69). The sealed volume of air enables the micro-speaker to produce sufficient levels of low frequency excitation of the eardrum. The configuration of utilizing the air volume between the junction box and the speaker versus vented air eliminates damage that could potentially results from leakage of water. This feature, therefore, permits the headset to be able to be operated in inclement environments.

In a preferred embodiment, for simplicity of operation, the stethoscope has a limited number of five fixed volume settings. In this embodiment, the setting in use is remembered so that during routine examinations, during which the power would be turned on and off while the chest piece is moved from place to place, the same volume setting comes up each time.

Figure 17:
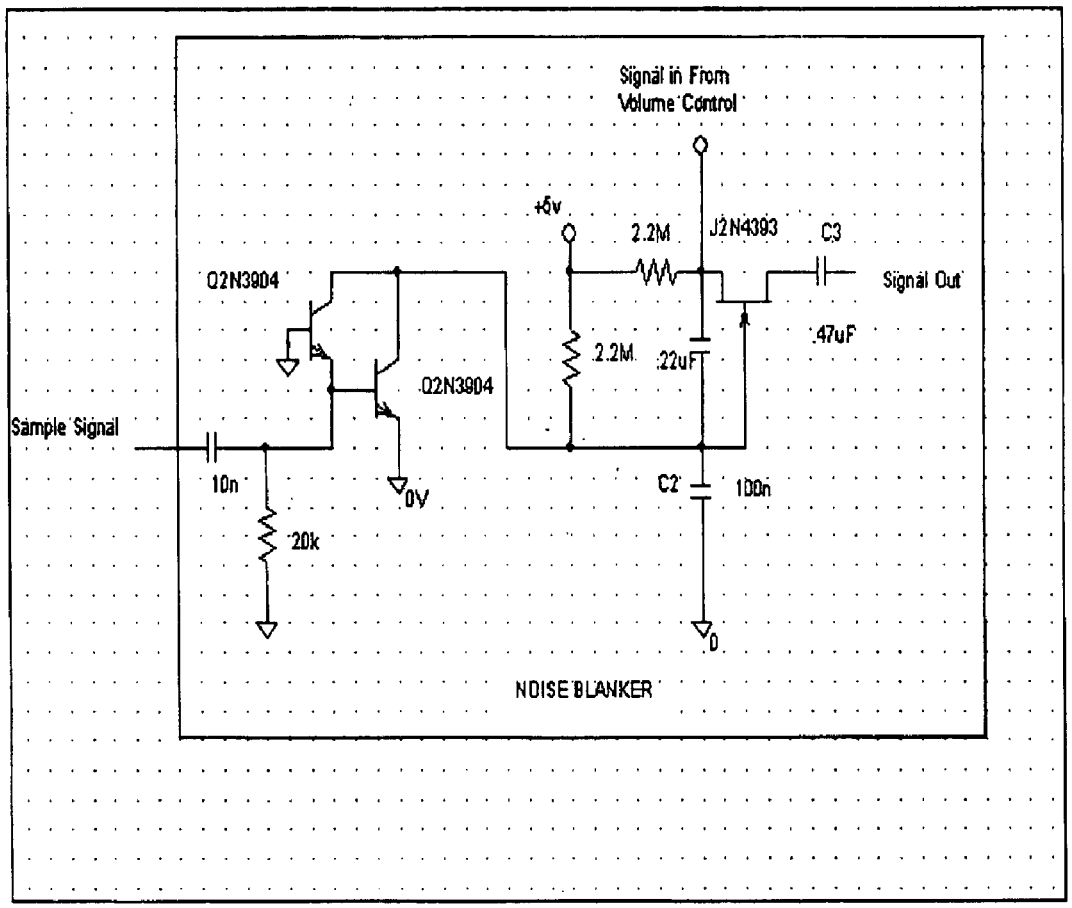
FIG. 17. Diagram of preferred noise blanking circuitry.

Additionally, in a preferred embodiment, the stethoscope contains hearing protection in the form of a noise blanking circuit. A preferred embodiment of this circuitry is illustrated in FIG. 17. This aspect would protect the user from discomfort or hearing damage if, for example, the chest piece was accidentally jarred or scraped across any surface, thereby generating very high levels of broadband noise within the sensor assembly. This circuitry provides a feature whereby the sound level is sampled at a point prior to the volume control. That means that the sound level that causes the output to be blanked is not dependent on the volume control. Additionally, the amplitude of sound that triggers blanking is frequency dependent. The lower the frequency, the larger the amplitude that is required to trigger blanking. This is advantageous because broadband noise containing energy at 1000 Hz that has the same amplitude as sound from a normal strong heart (for which the sound content does not significantly exceed 150 Hz) would be extremely annoying if not hazardous to the user. A simple RC filter pole is adjusted to achieve this frequency dependence and used as shown in FIG. 16 between the sound level sample point and the input to the actual blanker.

In another embodiment, a novel ergonomic feature of the inventive stethoscope is the use of audible rather than visual feed back to the user when using the controls. When the Diaphragm mode is selected, a short high-pitch tone is generated in the ear tips. Likewise, a short low-pitch tone is generated as the Bell mode is selected. When the user selects a higher volume setting, a short high pitch tone is generated in the ear tips. When the user selects a lower volume setting, a short low-pitch tone is generated. When at the highest (or lowest) volume setting, and the user tries to go beyond the limit, a high-low (or low-high) pitch sequence of two tones is generated to inform the user that the volume is at the extreme of the range. There is also a similar audible low battery warning.

Example 6

Evaluation of Preferred Embodiments of Inventive Stethoscope

A field evaluation was conducted of the above example of the acoustic-electronic stethoscope incorporating the preferred specific embodiments disclosed in Examples 1-5. In the study, sixteen health care professionals with extensive experience in auscultation compared the experimental inventive acoustic-electronic stethoscope against a conventional stethoscope in a high ambient noise environment. Users completed a survey assessment form following their hands-on evaluation. In the study each device was utilized an equal number of times. A Wilcoxon Sign Ranks Test showed a significant difference in ranked performance of the noise reduction stethoscope over a conventional device. All respondents commented that they would prefer the experimental acoustic-electronic stethoscope in a noisy environment. A summary of questionnaire results is shown in Table 1.

TABLE 1

| Issue commented on | Experimental Acoustic-Electronic Stethoscope | Conventional Stethoscope |
| --- | --- | --- |
| On improving ability to hear heart sounds in noise* | 75% strongly agree<br>25% agree<br>Median: strongly agree | 43% undecided<br>36% disagree<br>median: undecided |
| On improving ability to hear lung sounds in noise* | 94% strongly agree<br>6% agree<br>Median: strongly agree | 43% disagree<br>21% undecided<br>Median: disagree |
| On improving ability to determine BP in noise* | 46% strongly agree<br>36% agree<br>18% undecided** | 46% disagree<br>27% undecided*<br>Median: disagree |
| On improving quality of care in noise* | 73% strongly agree<br>27% agree<br>Median: strongly agree | 60% undecided<br>20% disagree<br>Median: undecided |
| On confidence in diagnosis* | 75% rated 80% confidence<br>12% rated 100% confidence<br>Median: 80% confidence | 40% rated 60% confidence<br>27% rated 40% confidence<br>Median response: 40% confidence |
| On ease of use (1 best to 4 worst)<br>No significant difference | 47% rated 1<br>53% rated 2<br>Median: 2 | 50% rated 1<br>36% rated 2<br>Median: 1.5 |
| On ability to reduce noise*<br>(1 best to 4 worst) | 81% rated 1<br>13% rated 2<br>Median: 1 | 67% rated 4<br>33% rated 3<br>Median: 4 |
| On ability to hear heart sounds*<br>(1 best to 4 worst) | 75% rated 1<br>25% rated 2<br>Median: 1 | 47% rated 3<br>40% rated 4<br>Median: 3 |
| On ability to hear lung sounds*<br>(1 best to 4 worst) | 94% rated 1<br>6% rated 2<br>Median: 1 | 40% rated 4<br>40% rated 3<br>Median: 3 |
| On ability to detect BP*<br>(1 best to 4 worst) | 60% rated 1<br>40% rated 2<br>Median: 1 | 50% rated 2<br>30% rated 4<br>Median: 2.5 |

*Significant at p less than .01
**Respondents who did not attempt BP may have indicted "Undecided" on device performance.

What is claimed is:

1. An electronic stethoscope comprising a chest piece having a diaphragm, operably connected to a sensor circuit board assembly, containing a top and a bottom surface and also having two piezoelectric polymer sensor elements with one mounted on and electrically connected to each of said top sensor circuit board assembly surface and the other mounted on and electrically connected to the bottom surface, such that vibrational energy impacting on said diaphragm results in dynamic strain on said piezoelectric polymer sensor elements and generation of an electrical signal to a signal output device, wherein sensor assembly contains a preamplifier circuit that provides high pass filtering that suppresses low frequency sounds below 50 Hz and that contains a difference amplifier that cancels common mode noise from the sensor assembly by subtracting the signals from said top and bottom piezoelectric polymer sensor elements.

2. The stethoscope of claim 1, wherein said sensor circuit board assembly contains grooves, wherein said grooves permit flexion of said assembly and flexion of said piezoelectric polymer sensor elements.

3. The stethoscope of claim 1, wherein said piezoelectric polymer sensor elements give rise to an electrical signal of opposite polarity when said sensor assembly is flexed.

4. The stethoscope of claim 1, wherein said signal output device is a binaural headset.

5. The stethoscope of claim 1, wherein said chest piece contains a contoured housing containing a grip for holding said chest piece.

6. The stethoscope of claim 1, wherein said chest piece contains an activation switch positioned such that pressing the chest piece to a patient causes activation of the stethoscope.

7. The stethoscope of claim 1, wherein audible feed back signals is provided to the user.

8. The stethoscope of claim 1, wherein said sensor circuit board assembly is electrically connected to a junction enclosure containing condition circuitry.

9. The stethoscope of claim 1, wherein said diaphragm is contained in a diaphragm retainer having a plurality of acoustic vent spaces around the periphery of said diaphragm retainer for the prevention of resonant amplification of sound.

10. The stethoscope of claim 1, wherein said diaphragm has a raised portion for contacting the skin and focusing vibrations.

11. The stethoscope of claim 1, wherein said diaphragm is operably connected to said sensor circuit board assembly via a coupling disk.

12. The stethoscope of claim 4, wherein said binaural head set comprises two ear assemblies with each of said assembly having an ear component containing an ear tip for insertion into the ear and an attachment component, electrically connected to said junction, and a micro-speaker in acoustic communication with the ear tip component via an airway extending lengthwise through the diameter of the assembly with said attachment component and earpiece component connected to form a water tight seal.

13. The stethoscope of claim 7, wherein said audible feed back signals are provided when the volume and band controls are used and when the batteries are low.

14. The stethoscope of claim 8, wherein said signal conditioning circuitry contains for bell and diaphragm modes.

15. The stethoscope of claim 8, wherein said signal condition circuitry contains noise-blanking circuitry with frequency-dependent sensitivity.

16. The stethoscope of claim 8, wherein said connection of said junction enclosure to said chest piece also contains an output jack such than an electrical connection to a data recording device can be made.

17. The stethoscope of claim 9, wherein said diaphragm retainer is made of a nonmetallic material.

18. The stethoscope of claim 9, wherein said chest piece is acoustically unbounded.

19. The stethoscope of claim 9, wherein said chest piece contains a seal membrane adjacent to said bottom surface of said sensor assembly forming a water-tight seal between an interior compartment of said chest piece, bounded by said seal membrane and the chest piece housing and containing within it said sensor assembly, and an exterior compartment, bounded by said diaphragm, said seal membrane and the inside periphery of said diaphragm retainer.

20. The stethoscope of claim 10, wherein said raised portion is circular.

21. The stethoscope of claim 11, wherein said coupling disk impinges on the center of the bottom surface of said sensor assembly such that energy from the diaphragm via the coupling disk causes flexion of said sensor circuit board assembly and said piezoelectric polymer sensor elements.

22. The stethoscope of claim 12, wherein compliant air is provided by air volume behind said speaker and wherein said speaker is not vented to the outside.

23. The stethoscope of claim 12, wherein said ear tips are coaxial when the headset is expanded and inserted into the ears.

24. The stethoscope of claim 12, wherein said headset is watertight.

25. The stethoscope of claim 12, wherein said ear tips are coaxial when said head set is expanded such that the tips are 13.0 cm apart.

26. The stethoscope of claim 14, wherein when said bell mode is used the high pass filter has a −3 dB frequency cut off of 55 to 65 Hz and when said diaphragm mode is used the filter has a cut off frequency of 90 to 100 Hz.

27. The stethoscope of claim 16, wherein said output jack is watertight.

* * * * *